(12) United States Patent
Barmaimon et al.

(10) Patent No.: US 11,590,279 B2
(45) Date of Patent: Feb. 28, 2023

(54) CLOCK MECHANISM FLOW REGULATOR

(71) Applicant: FLEX LTD., Singapore (SG)

(72) Inventors: Eyal Barmaimon, Haifa (IL); Lior Shtram, Haifa (IL); Shai Finkman, Haifa (IL)

(73) Assignee: FLEX LTD., Singapore (SG)

( * ) Notice: Subject to any disclaimer, the term of this patent is extended or adjusted under 35 U.S.C. 154(b) by 955 days.

(21) Appl. No.: 16/006,188

(22) Filed: Jun. 12, 2018

(65) Prior Publication Data

US 2019/0022312 A1    Jan. 24, 2019

Related U.S. Application Data

(60) Provisional application No. 62/535,083, filed on Jul. 20, 2017.

(51) Int. Cl.
*A61M 5/145* (2006.01)
*A61M 5/315* (2006.01)
(Continued)

(52) U.S. Cl.
CPC ...... *A61M 5/1454* (2013.01); *A61M 5/16877* (2013.01); *A61M 5/20* (2013.01);
(Continued)

(58) Field of Classification Search
CPC .......... A61M 2005/14506; A61M 2005/2073; A61M 2005/2086; A61M 2005/3143; A61M 5/1452; A61M 5/1454; A61M 5/16877; A61M 5/31501; A61M 2205/8225; A61M 2205/8275; A61M 2205/8281; A61M 2205/8287;
(Continued)

(56) References Cited

U.S. PATENT DOCUMENTS 3,384,080 A   5/1968  Muller
4,300,554 A  11/1981  Hessberg et al.
(Continued)

FOREIGN PATENT DOCUMENTS

CN    104592755 A    5/2015
CN    204411425 U    6/2015
(Continued)

*Primary Examiner* — Shefali D Patel
(74) *Attorney, Agent, or Firm* — Volpe Koenig

(57) ABSTRACT

An automatic injection device with flow regulation is disclosed. The automatic injection device has an insertion needle configured to be inserted into a patient and a drug container which contains a pharmaceutical product and includes a plunger. The automatic injection device also has a fluid path which fluidly connects the drug container to the patient via the insertion needle, a potential energy source, and a regulator configured to restrict release of potential energy and restrict linear movement of the plunger and the pharmaceutical product into the fluid path at a proscribed pace. The regulator includes a clock escapement mechanism. The potential energy source may be a spring that surrounds the drug container and may be magnetically coupled to the plunger. The clock escapement mechanism is configured to control the spring at a regulated rate over a time interval using a gearbox and a rotational-to-linear translator comprising a rack and a pinion.

7 Claims, 4 Drawing Sheets

(51) Int. Cl.
*A61M 5/20* (2006.01)
*A61M 5/168* (2006.01)
*A61M 5/31* (2006.01)
*A61M 5/142* (2006.01)

(52) U.S. Cl.
CPC ........ *A61M 5/315* (2013.01); *A61M 5/31501* (2013.01); *A61M 5/14248* (2013.01); *A61M 5/14526* (2013.01); *A61M 5/31511* (2013.01); *A61M 5/31515* (2013.01); *A61M 2005/14506* (2013.01); *A61M 2005/2086* (2013.01); *A61M 2005/3143* (2013.01); *A61M 2205/0288* (2013.01); *A61M 2205/8275* (2013.01); *A61M 2205/8281* (2013.01); *A61M 2205/8287* (2013.01)

(58) Field of Classification Search
CPC ......... A61M 5/14244; A61M 5/14248; A61M 5/145; A61M 5/14526; A61M 5/20; A61M 5/315; A61M 5/31511; A61M 5/31515; A61M 2005/31518; A61M 2005/3152; A61M 2205/0272; A61M 2205/0288
See application file for complete search history.

(56) References Cited

U.S. PATENT DOCUMENTS

| | | | |
|---|---|---|---|
| 4,865,229 A | 9/1989 | Schneider et al. | |
| 9,594,349 B2 | 3/2017 | Stranczl et al. | |
| 2005/0197625 A1 | 9/2005 | Haueter et al. | |
| 2012/0172804 A1 | 7/2012 | Plumptre | |
| 2015/0297827 A1 | 10/2015 | Hanson et al. | |
| 2017/0290975 A1* | 10/2017 | Barmaimon | A61M 5/31515 |

FOREIGN PATENT DOCUMENTS

| | | |
|---|---|---|
| CN | 106267459 A | 1/2017 |
| CN | 106267549 A | 1/2017 |
| CN | 106421978 A | 2/2017 |
| EP | 0 110 117 A2 | 6/1984 |
| FR | 2608929 A1 | 7/1988 |
| SU | 1122326 A1 | 11/1984 |
| WO | 2008/142394 A1 | 11/2008 |
| WO | 2012/072555 A1 | 6/2012 |
| WO | 2013/026850 A1 | 2/2013 |
| WO | 2014001310 A1 | 1/2014 |
| WO | 2015059192 A1 | 4/2015 |
| WO | 2015/139775 A1 | 9/2015 |
| WO | 2017007952 A1 | 1/2017 |

* cited by examiner

CLOCK MECHANISM FLOW REGULATOR

PRIORITY CLAIM

This application claims priority under 35 U.S.C. § 119 to U.S. Provisional Application No. 62/535,083, filed on Jul. 20, 2017 which is expressly incorporated by reference herein in its entirety.

SUMMARY

The present disclosure is directed to flow regulation of an automatic injection device. The automatic injection device includes an insertion needle configured to be inserted into a patient and a drug container which contains a pharmaceutical product and includes a plunger. The automatic injection device also includes a fluid path which fluidly connects the drug container to the insertion needle, a potential energy source, and a regulator configured to cause a predefined, possibly linear movement of the plunger to force the pharmaceutical product into the fluid path at a proscribed pace. The potential energy source may be a spring that surrounds the drug container and may be magnetically coupled to the plunger. The regulator includes a clock escapement mechanism. The clock escapement mechanism applies a counterforce and thus restricts movement of the spring and plunger in a controlled rate over a specified time interval, using a gearbox and a rotational-to-linear translator.

DETAILED DESCRIPTION OF THE PREFERRED EMBODIMENTS

Figure 1:
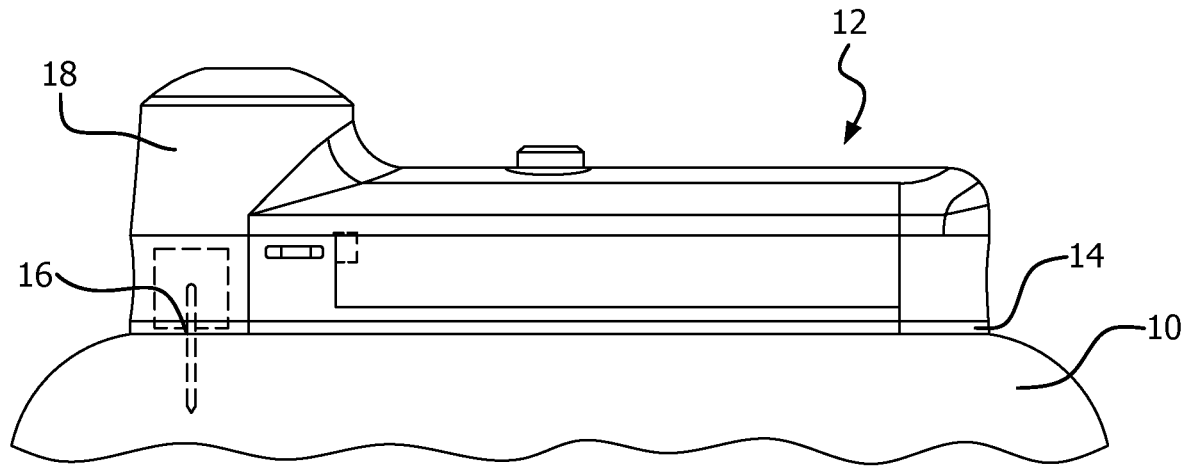
FIG. 1 is a side view illustration of an exemplary automatic injection device positioned on a patient.

Injection devices are used to deliver pharmaceutical products such as biologics and medications to a patient (i.e., a person or animal). A syringe and needle is an example of a widely-used injection device. This basic system typically involves a person manually moving a plunger portion of the syringe to force the pharmaceutical product through the needle and into the patient. Other injection devices have been developed to deliver pharmaceutical products automatically at the touch of a button or the actuation of a switch. These devices are advantageous in that they allow a patient to more easily self-administer the pharmaceutical product. Moreover, some automatic injection devices allow for slow or periodic delivery of the pharmaceutical product as needed, which is a typical procedure for patients dependent on insulin injections, for example. However, there is a need for automatic injection devices to provide increased injection control in a compact device such that the device is easy to handle and discrete for a patient who may wear the device for an extended period of time.

Disclosed embodiments pertain to a regulator for an automatic injection device. For example, the regulator may be configured to control movement of a plunger placed in a drug container. Further movement of the plunger inside the drug container pushes the pharmaceutical product through a fluid path and to an insertion needle which connects to the patient. This controlled movement of the plunger allows for metered delivery of the pharmaceutical product according to desired parameters.

The disclosed regulator includes features which allow for precise control over plunger movement which is based on stored potential energy while providing a small form factor which allows the automatic injection device to be compact. The disclosed regulator utilizes a clock escapement mechanism and a potential energy source in order to control movement of the plunger. In the embodiment set forth in the drawings and as described hereinafter, the potential energy source is a spring that may push the plunger magnetically or may directly push the connected plunger; but that is just by way of example. In other embodiments, any potential energy source may be utilized, including compressed air.

Current energy sources for automatic injection devices utilize springs as an energy source for pumping the pharmaceutical product out of the device and into a patient. These springs, however, apply a variable force because the force of the spring is relative to its displacement. This varies the velocity and rate of infusion.

In contrast, the described embodiments regulate potential energy in a proscribed regulated pace. In the embodiment set forth in the drawings and as described hereinafter, the disclosed regulator includes a mechanical clock escapement mechanism that restricts movement of the spring over a specified period of time for more restricted and controlled release. Thus, the clock escapement mechanism controls the plunger so that the velocity of the potential energy source and rate of infusion is constant. This configuration allows for a cost-effective, space saving alternative to control the movement of the plunger with a passive, mechanical driving device. This configuration, when totally mechanical, can undergo sterilization procedures that a unit with electronics may not be able to utilize.

It should be understood that other types of regulators may be used in place of a clock mechanism, and one of skill in the art may utilize other mechanical mechanisms in order to restrict and regulate the movement of the plunger. In some embodiments, the clock escapement mechanism may be connected to a device which further regulates the spring over a specified time interval. This restriction of movement of the spring may restrict movement of the plunger and thus movement of the pharmaceutical product out of the drug container over time (e.g., and into a patient through a fluid path).

FIG. 1 is a depiction of an exemplary embodiment of an automatic injection device 12 on a patient 10. The patient 10 is not limited and can be any organism which may receive an injection. The device 12 is configured to deliver a pharmaceutical product to the patient 10 automatically. This means that the device 12 is controlling the injection in some way such that the system differs from other injection systems where manual input alone causes the injection (i.e., a conventional syringe and needle system or other available systems). The automatic aspect of the device 12 may additionally or alternatively relate to the duration of the injection, controlled injection intervals, a delay between input and injection, etc.

The device 12 includes a base 14 that contacts the patient's skin. The device 12 includes an insertion needle 16 which enters a patient to deliver a pharmaceutical product, such as insulin, to the patient. An example of an automatic injection device which includes many of the features that may be incorporated into the device 12 is described in WO 2017/007952, which is herein incorporated by reference. However, it should be understood that the device 12 is not limited to the automatic injection device described therein or the exemplary embodiments described below. An automatic injection device consistent with this disclosure may include some of the features described herein but is not limited thereto. For example, a disclosed automatic injection device may resemble a syringe and needle system or other injection system, which is adapted for automatic injections via the features described herein.

Figure 2:
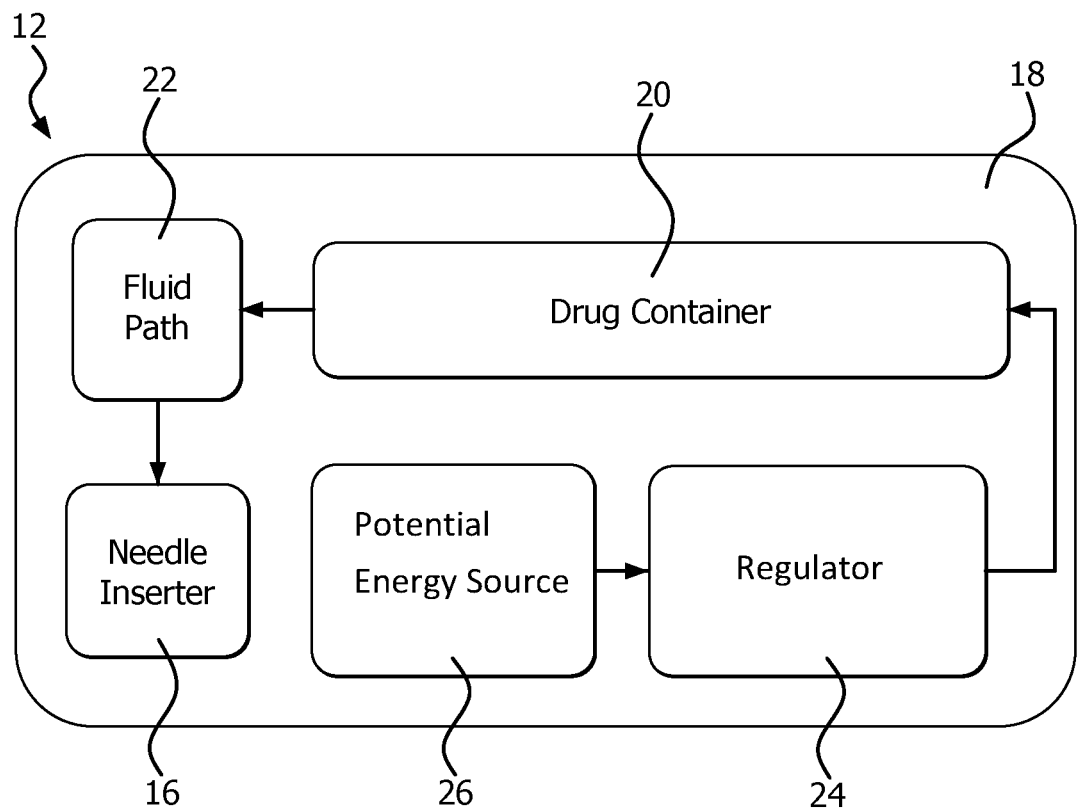
FIG. 2 is a schematic illustration of the components of an automatic injection device consistent with disclosed embodiments.

FIG. 2 is a schematic illustration of the automatic injection device 12 and flow regulator 24 and the basic features of the device 12 which facilitate automatic injections of a pharmaceutical product into the patient 10. The device 12 preferably includes a housing 18 which holds at least some of the features of the device 12. In addition to the insertion needle 16, these features preferably include a drug container 20, a fluid path 22, a regulator 24 and potential energy source 26. These features work in conjunction with each other to automatically and mechanically deliver a pharmaceutical product to the patient 10 according to desired parameters.

The regulator 24 provides the automatic aspect of the injections via device 12. For example, the regulator 24 is a mechanical system which restricts movement of the pharmaceutical product from the drug container 20 to the fluid path 22 and ultimately into the patient 10 at a proscribed pace. In the embodiment described in the drawings and hereinafter, the regulator 24 mechanically regulates movement of a plunger (not depicted). In other embodiments, the regulator 24 may include both a mechanical unit and a small electrical unit that may exert a minimal amount of energy for regulating movement of the plunger and release of the fluid at a proscribed pace. For example, in one embodiment, the regulator 24 may include a ratchet mechanism that releases potential energy from the potential energy source at a certain pace and exerts a small fraction of energy in order to stop the mechanism in a required pace. The ratchet may be stopped and released by a small electrical unit such as a solenoid or a different actuator. In addition, in another embodiment, the regulator may control the flow between the needle and the fluid path by periodically obstructing fluid flow.

The drug container 20 is a containing element which supplies the pharmaceutical product. The drug container 20 may be a vial, syringe, or the like and includes a space for containing the pharmaceutical product, which is not limited to a particular substance. The pharmaceutical product may be any substance which is considered one or more of a drug, biologic, medication, or placebo, for example. The drug container 20 is preferably a hollow cylindrical tube which receives the pharmaceutical product. However, it should be understood that other configurations are possible.

In the device 12, the drug container 20 is fluidly connected to the insertion needle 16 by the fluid path 22. The fluid path 22 may be a physical connecting channel which serves as a conduit for delivering the pharmaceutical product from the drug container 20 to the insertion needle 16 and ultimately into the patient 10. The fluid path 22 may include additional structure, including actuating mechanisms which initiate delivery of the pharmaceutical product and/or control mechanisms which meter an amount of product which is delivered to the patient 10 at any particular time. The fluid path 22 may include an element or mechanism which is configured to establish the connecting channel, such as a puncturing needle or the like. The fluid path 22 may be associated with a mechanical start button or control switch which control an element of the fluid path 22 (e.g., a valve) in order to start or stop the delivery of the pharmaceutical product. It should be understood, however, that the fluid path 22 may be a passive system component in at least some embodiments.

Figure 3:
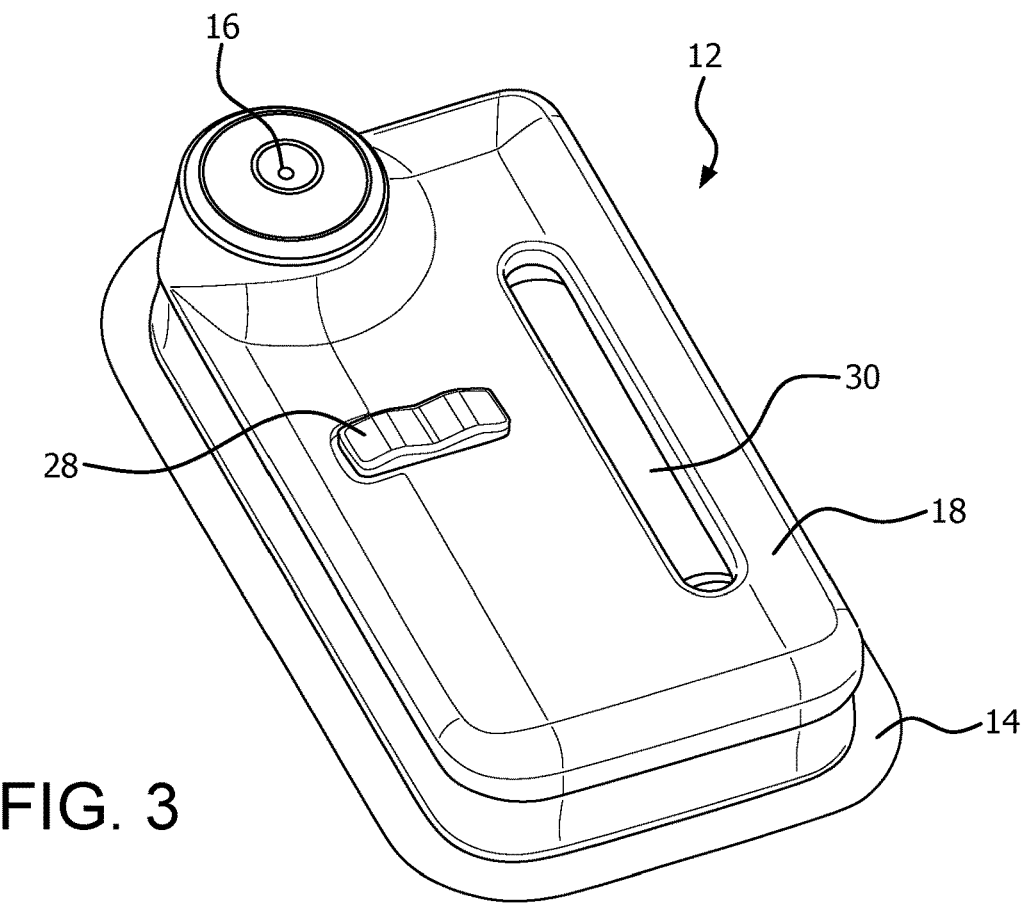
FIG. 3 is a perspective view of a top side of the automatic injection device.
Figure 4:
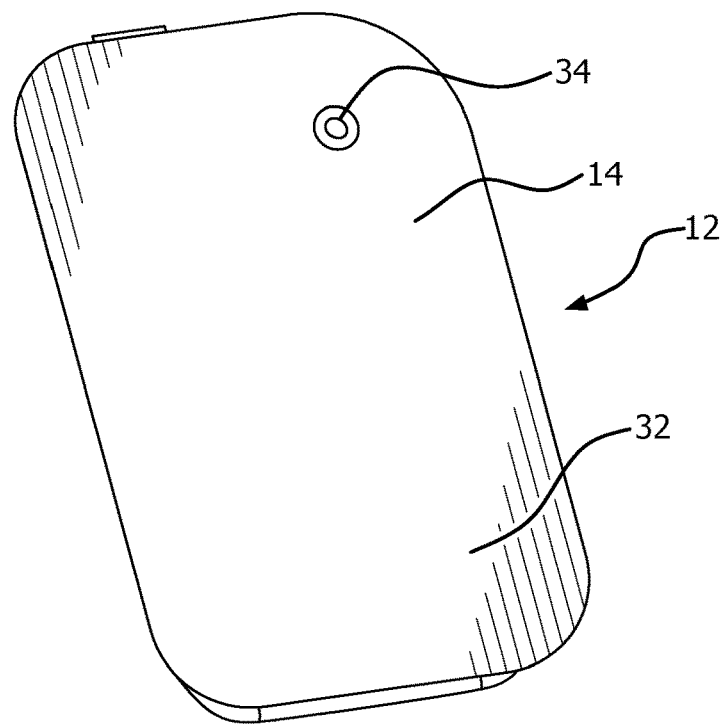
FIG. 4 is a perspective view of a bottom side of the automatic injection device.

FIGS. 3 and 4 further illustrate an exemplary embodiment of the automatic injection device 12. FIG. 3 illustrates a first side of the device 12, including the housing 18 which rests on top of the base 14. The housing 18 is illustrated as being rectangular, but can include any shape. The housing 18 may include optional features such as a window 30 which provides a view of the drug container 20 and thus the current fluid level.

FIG. 4 illustrates a second side of the device 12 including a bottom surface of the base 14. The bottom surface 32 includes an opening 34 for receiving the insertion needle 16. In use, the device 12 is placed against the patient 10 with the bottom surface 32 of the base 14 against the skin. An injection needle extends through the opening 34 and into the patient 10 to deliver the pharmaceutical product. The bottom surface 32 may include an adhesive material thereon to adhere the device 12 to the patient 10 for either a short or long period of time, depending on the particular use of the device 12.

Figure 5:
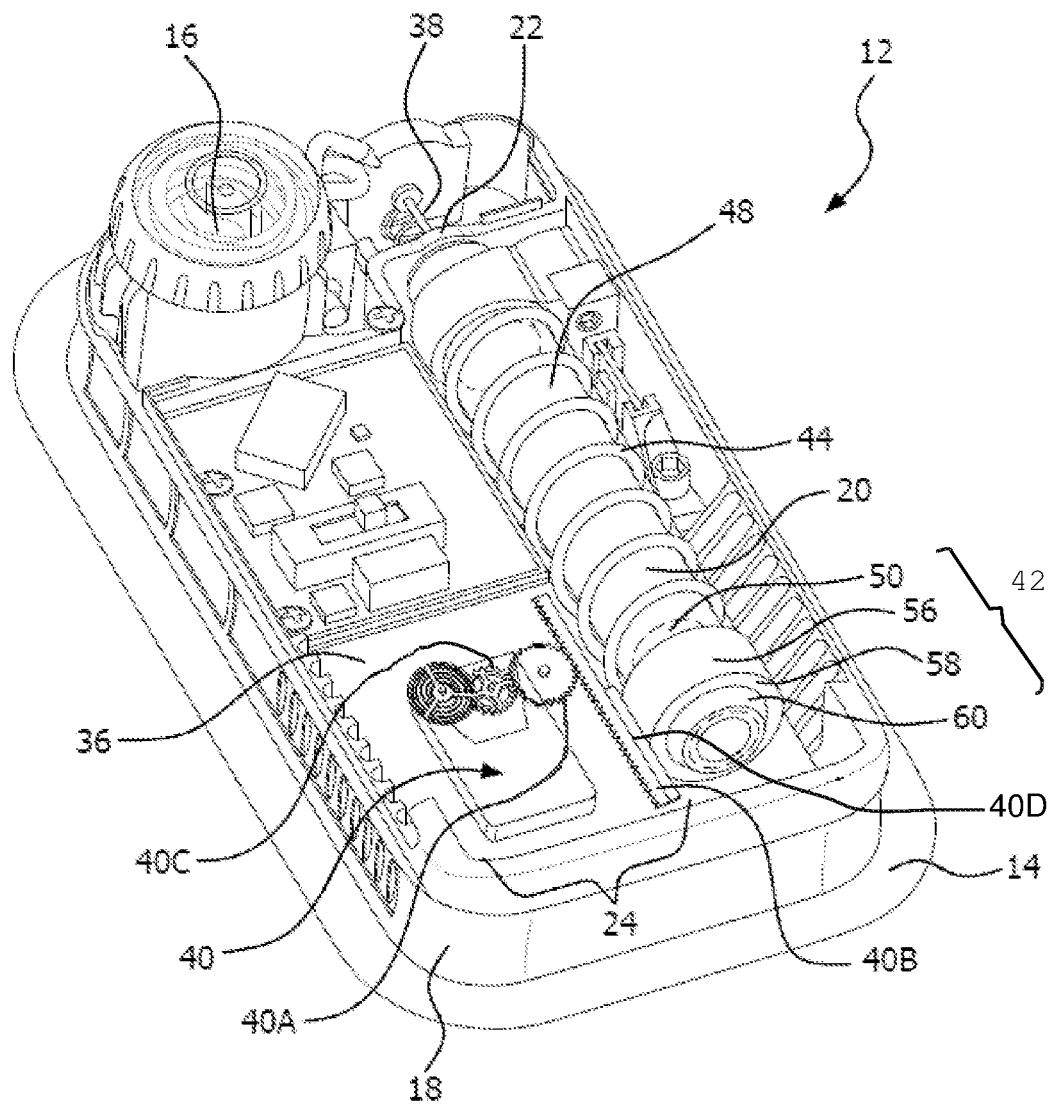
FIG. 5 is a perspective view of the internal components according to an embodiment of the automatic injection device.

FIG. 5 illustrates the device 12 incorporating the flow regulator 24 with the top portion of the housing 18 removed such that the internal features are shown in an enclosed space 36 formed by a lower portion of the housing 18 and the base 14. The device 12 includes exemplary embodiments of the insertion needle 16, the drug container 20, the fluid path 22, and the regulator 24. The enclosed space 36 houses at least the drug container 20 and the regulator 24 such that the elements are positioned inside of the housing 18.

The fluid path 22 in this embodiment includes a connector 38 which physically connects to the drug container 20 to establish a connection channel between the interior of the drug container 20 and the insertion needle 16. In the illustrated embodiment, the insertion needle 16 is positioned perpendicular to the drug container 20 such that the path of the pharmaceutical product is to travel out of the drug container 20 and laterally into the area of the insertion needle 16 via the fluid path 22. The pharmaceutical product subsequently travels vertically downward through the insertion needle 16 and into the patient 10. This configuration is exemplary, however, and the disclosed embodiments are not limited thereto. In other embodiments, the insertion needle 16 may be aligned in the same direction as the drug container 20 and/or the fluid path 22.

In the present embodiment, the regulator 24 includes a clock escapement mechanism 40. The clock escapement mechanism 40 includes a set of gears 40A, a pinion 40C, connected to a rotational-to-linear translator 40B. In one embodiment, the clock escapement mechanism 40 inhibits movement of the spring 44 via the gears 40A, the pinion 40C, and the linear translator 40B, by applying a counterforce to the spring 44. The gears 40A and the pinion 40C may be coupled to each other and to the linear translator 40B, and engages and moves the linear translator 40B in a linear motion. The linear translator 40B must therefore be configured to convert rotational motion from the gears 40A and the pinion 40C into a linear motion when a counterforce is applied. In one embodiment, the linear translator 40B may include a rack 40D. The gears 40A and pinion 40C may engage with the teeth of the rack and pinion of the linear translator 40B such that rotational movement of the gears moves the linear translator 40B in increments as the teeth of the gears engage with each other. The movement of the linear translator 40B controls and restricts movement of the spring 44 along the drug container 20, which controls and restricts movement of the plunger 50 in a linear motion inside the drug container 20.

In the embodiments set forth in the drawings and described hereinafter, the spring 44 is positioned outside of the drug container 20 and is not connected directly to the plunger 50, but this is just by way of example. The clock escapement mechanism 40 is configured to slowly allow the spring 44 to return to a resting position over a specified time interval. In the process of returning to a resting position, the spring 44 pushes the plunger 50 incrementally, toward a second longitudinal end 48 of the drug container 20, thereby forcing the pharmaceutical product into the fluid path 22 and ultimately delivering it to the patient 10 through the insertion needle 16 in a controlled manner over the specified time interval, as needed.

In the embodiment as set forth in the drawings and described hereinafter, movable elements 42 control the movement of the plunger 50 such that the spring 44 moves and magnetically pushes the plunger 50 in a proscribed rate, but that is just by way of example. It should be noted that in other embodiments, other mechanisms for connecting the spring 44 and the plunger 50 to control movement may be utilized.

In the present embodiment, the movable elements 42 include an outer collar 56, an outer magnet 58, and an inner magnet 60. The outer magnet 58 and inner magnet 60 translates movement of the outer collar 56 into movement of the plunger 50. The outer magnet 58 surrounds the exterior of the drug container 20. The outer collar 56 may be generally formed of a soft magnetic alloy. In an exemplary embodiment, the outer collar 56 is in contact with a first end of the spring 44. Extension and retraction of the spring 44 thus causes corresponding linear movement of the outer collar 56 along an axis of the drug container 20. The outer collar 56 and outer magnet 58 may be attached to each other, such as through magnetic attraction, friction fit, adhesive, fasteners, etc. In an alternative embodiment, the outer collar 56 and the outer magnet 58 may be the same component (e.g., the outer collar 56 is diametrically magnetized or includes a magnetized portion).

The inner magnet 60 is generally cylindrical and may be solid or in the form of a ring. Other shapes of the inner magnet 60 are also possible (e.g., U-shaped, spherical, square, etc.) The inner magnet 60 is sized to fit within the drug container 20 and abuts a first side of the plunger 50. In an alternative embodiment, the inner magnet 60 and the plunger 50 are the same component (e.g., the plunger 50 is diametrically magnetized or includes a magnetized portion).

The outer magnet 58 and inner magnet 60 are configured to create a magnetic field which maintains a relative position between the two. For example, the outer magnet 58 may include a first outer magnet and a second outer magnet that are diametrically magnetized in opposite directions of each other. The first outer magnet and the second outer magnet may each be diametrically magnetized with a first radial side being a first pole and a second radial side being a second pole. The inner magnet 60 may include a first inner magnet and a second inner magnet that are diametrically magnetized in opposite directions with each other. The first inner magnet and the second inner magnet may each be diametrically magnetized with a first radial side being a first pole and a second radial side being a second pole. The first inner magnet may be diametrically magnetized in a direction opposite from the first outer magnet, and the second inner magnet may be diametrically magnetized in a direction opposite from the second outer magnet.

For example, the first inner magnet may include a first radial side which is aligned with the first radial side of the first outer magnet and which is an opposite pole of the first radial side of the first outer magnet. Similarly, the first inner magnet may include a second radial side which is aligned with the second radial side of the first outer magnet and which is an opposite pole of the second radial side of the first outer magnet. In this way, the first side of the first outer magnet is attracted to the first side of the first inner magnet and the second side of the first outer magnet is attracted to the second side of the first inner magnet. In addition, the second inner magnet may include a first radial side which is aligned with the first radial side of the second outer magnet and which is an opposite pole of the first radial side of the second outer magnet. Similarly, the second inner magnet may include a second radial side which is aligned with the second radial side of the second outer magnet and which is an opposite pole of the second radial side of the second outer magnet. In this way, the first side of the second outer magnet is attracted to the first side of the second inner magnet and the second side of the second outer magnet is attracted to the second side of the second inner magnet. With this configuration, the first inner magnet can be positioned in the through-hole of the first outer magnet and the second inner magnet can be positioned in the through-hole of the second outer magnet in equilibrium, such that the inner magnet 60 will follow movement of the outer magnet 58.

The outer magnet 58 is positioned around the exterior of the drug container 20, in alignment with the inner magnet 60. The outer collar 56 surrounds the outer magnet 58 (or is the outer magnet 58 in alternative embodiments). The spring 44 surrounds the drug container 20 and is operatively coupled to the outer magnet 58 and outer collar 56. The spring 44 may be positioned on either side of the outer collar 56. Movement of the outer collar 56 therefore causes corresponding linear movement of the outer magnet 58. In this way, the spring 44 is configured to cause linear movement of the outer magnet 58 along an outside of the drug container 20, in a longitudinal direction of the drug container 20 (i.e., along a longitudinal axis of the drug container 20). Movement of the outer magnet 58 outside of the drug container causes corresponding movement of the inner magnet 60 inside the drug container without physically breaking a barrier into the drug container. In this configuration, the spring 44 moves the inner magnet 60 (via the outer magnet 58 and outer collar 56) incrementally, which pushes the plunger 50 toward the second longitudinal end 48 of the drug container 20, thereby forcing the pharmaceutical product into the fluid path 22 and ultimately delivering it to the patient 10 through the insertion needle 16 in a controlled manner over the specified time interval, as needed.

Figure 6:
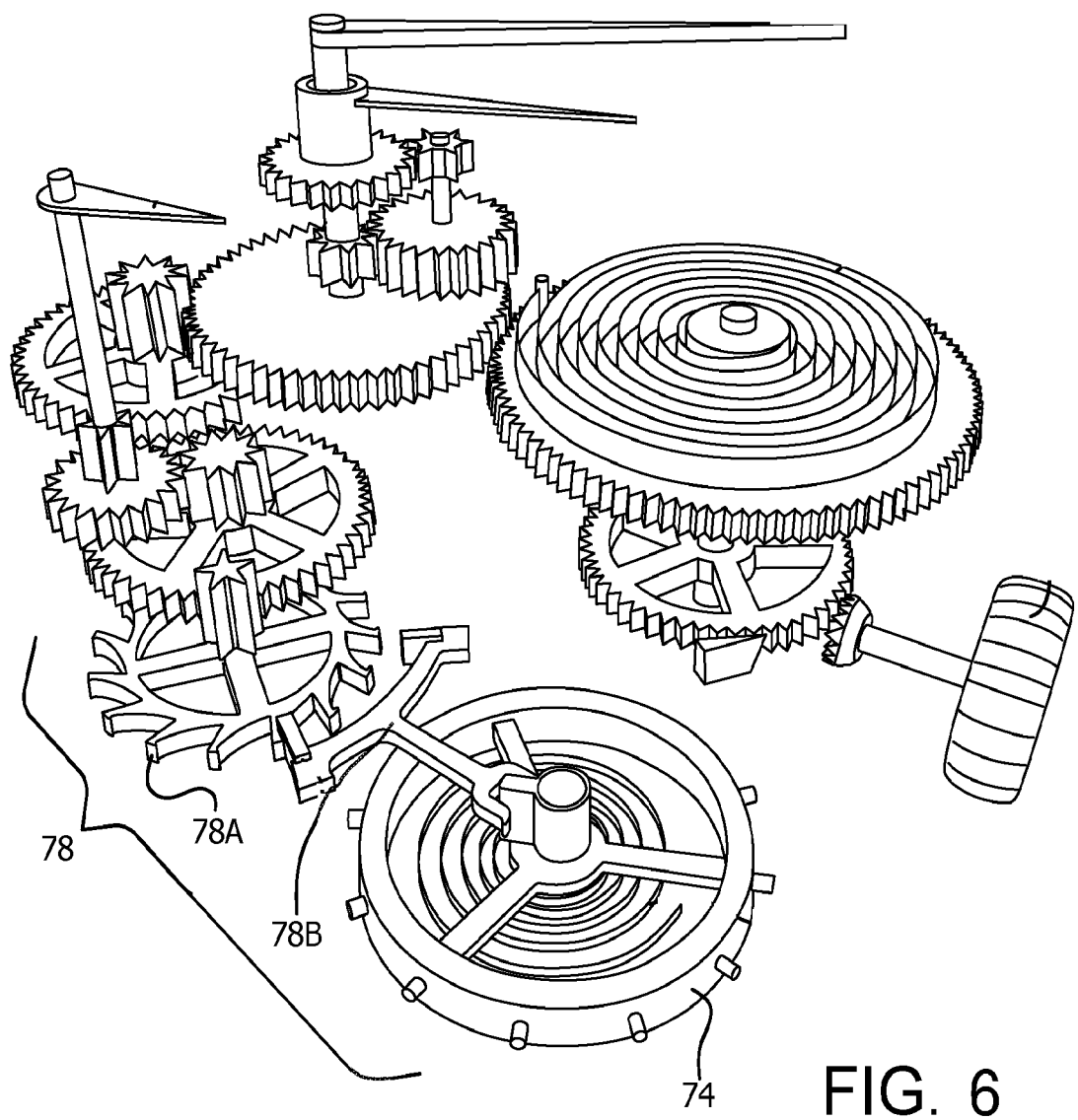
FIG. 6 is a perspective view of the internal components of a clock, incorporated in an embodiment of the clock escapement mechanism for the regulator.

FIG. 6 is a perspective view of the internal components of a clock incorporated in an embodiment of the clock mechanism 40 for the regulator 24. Components of the escapement mechanism of the clock may be similar to the clock escapement mechanism 78, which includes an escape wheel 78A and a pallet 78B. In the present embodiment, the clock escapement mechanism 78 further regulates the periodic movement of the pinion 40C (not depicted), while the balance wheel 74 is operatively coupled to the escapement mechanism 78 via the pallet 78B.

When the spring 44 begins to move, the escapement mechanism 78, the balance wheel 74, the gears 40A, and the pinion 40C begin to move. As the balance wheel 74 moves rotationally, clockwise and counterclockwise periodically, the movement releases a tooth of the escape wheel 78A of the escapement mechanism 78. The release of the tooth of the escape wheel 78A allows the gear 40A and the pinion 40C (not depicted) to only advance by a fixed amount. This regular periodic advancement moves the gear 40A, the pinion 40C, and the rack 40D in a controlled and restricted manner. This control also restricts movement of the spring 44 (not depicted) over a time interval. This configuration enables delivery of the pharmaceutical product at a more controlled rate over a specified time.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. An automatic injection device, comprising:
    a drug container which contains a pharmaceutical product, the drug container including a plunger;
    a fluid path which connects the drug container to an insertion device;
    an outer magnet and an inner magnet, the outer magnet located on an exterior portion of the drug container and the inner magnet located within the drug container;
    a spring surrounding the exterior portion of the drug container and connected to an outer collar comprising the outer magnet, wherein extension and retraction of the spring causes a linear movement of the outer magnet and the linear movement of the outer magnet causes corresponding movement of the inner magnet, and the inner magnet moves the plunger and forces the pharmaceutical product into the fluid path; and
    a regulator comprising:
        a clock escapement mechanism comprising at least one set of gears, and
        a linear translator comprising a rack and a pinion;
    wherein the linear translator is configured to convert a rotational movement of the at least one set of gears and the pinion into a linear motion of the rack,
    the clock escapement mechanism applies a counterforce to the spring to restrict release of potential energy from the spring over a proscribed period of time, and
    the at least one set of gears is configured to move upon movement of the spring.

2. The automatic injection device of claim 1, wherein the at least one set of gears comprises:
    a pallet and an escape wheel gear configured to restrict a regular periodic movement of the pinion by a fixed amount that restricts release of the potential energy over a time interval.

3. The automatic injection device of claim 2, wherein the clock escapement mechanism further comprises a balance wheel.

4. The automatic injection device of claim 1, wherein the spring is indirectly connected to the plunger and moves the plunger magnetically.

5. The automatic injection device of claim 1, wherein the spring is mechanically coupled to the at least one set of gears via the rack.

6. The automatic injection device of claim 1, wherein the linear translator moves along the drug container.

7. The automatic injection device of claim 1, wherein the regulator further comprises an electric circuit that measures time and controls restrictor intervals.

* * * * *